United States Patent [19]

Rochat et al.

[11] Patent Number: 5,973,146
[45] Date of Patent: *Oct. 26, 1999

[54] PROCESS FOR THE PREPARATION OF AMINATED DIKETOBIS (ARYL OR HETEROARYL)PYRROLOPYRROLES AND THE USE THEREOF AS PHOTOCONDUCTIVE SUBSTANCES

[75] Inventors: Alain Claude Rochat, Fribourg; Olof Wallquist, Marly; Abul Iqbal, Arconciel; Jin Mizuguchi, Fribourg, all of Switzerland

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/128,332

[22] Filed: Sep. 29, 1993

Related U.S. Application Data

[63] Continuation of application No. 08/047,886, Apr. 15, 1993, abandoned, which is a continuation of application No. 07/381,212, Jul. 17, 1989, abandoned.

[30] Foreign Application Priority Data

Jul. 20, 1988 [CH] Switzerland ............................ 2769/88

[51] Int. Cl.[6] .................................................. C07D 487/04
[52] U.S. Cl. ............................ 544/144; 544/61; 544/131; 544/360; 544/373; 546/187; 546/193; 546/194; 546/199; 548/255; 548/262; 548/336; 548/378; 548/453
[58] Field of Search ...................................... 546/193, 194, 546/199, 187; 548/255, 262, 336, 378, 453; 544/61, 131, 144, 360, 373

[56] References Cited

U.S. PATENT DOCUMENTS

| | | | |
|---|---|---|---|
| 3,484,487 | 12/1969 | Dix | 260/577 |
| 4,415,685 | 11/1983 | Iqbal et al. | 524/92 |
| 4,579,949 | 4/1986 | Rochat et al. | 546/167 |
| 4,632,893 | 12/1986 | Rochat et al. | 430/58 |

*Primary Examiner*—Fiona T. Powers
*Attorney, Agent, or Firm*—Kevin T. Mansfield; Michele A. Kovaleski

[57] ABSTRACT

A process for the preparation of compounds of formula I

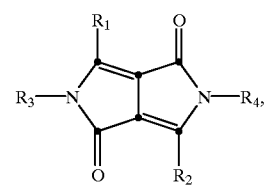

(I)

by reacting a pyrrolopyrrole of formula

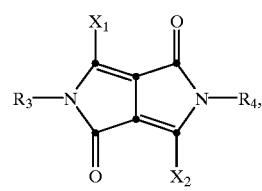

(II)

wherein $X_1$ is a group selected from

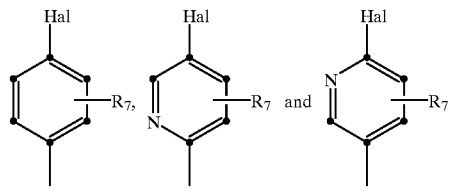

$X_2$ is a group selected from

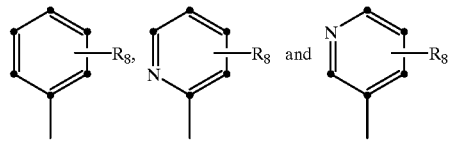

or has the same meaning as $X_1$, with a secondary amine of formula

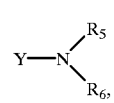

(III)

in the molar ratio 1:2, in the presence of an anhydrous dipolar aprotic solvent and of an amount 0.1 to 15 times in excess of stoichiometric proportion, based on the amine of formula III, of an anhydrous organic base, in the temperature range from 50° to 230° C. and under a pressure from 0 to 10 bar.

The substituents $R_1$ to $R_8$, Y and Hal are as defined in claim 1.

The compounds of formula I are especially suitable for use as photoconductive substances.

6 Claims, No Drawings

PROCESS FOR THE PREPARATION OF AMINATED DIKETOBIS (ARYL OR HETEROARYL)PYRROLOPYRROLES AND THE USE THEREOF AS PHOTOCONDUCTIVE SUBSTANCES

This is a continuation of application Ser. No. 08/047,886, filed on Apr. 15, 1993, now abandoned, which is a continuation of application Ser. No. 07/381,212, filed on Jul. 17, 1989, also abandoned.

The present invention relates to a process for the amination of 1,4-diketo-3,6-bis(aryl or heteroaryl)pyrrolo[3,4-c]pyrroles and to the use thereof as photoconductive substances.

1,4-Diketo-3,6-bis(aryl)pyrrolo[3,4-c]pyrroles, including aminoaryl derivatives, are disclosed, for example, in U.S. Pat. Nos. 4,415,685 and 4,579,949. Such aminoaryl derivatives of 1,4-diketopyrrolo[3,4-c]pyrroles can only be prepared by the hitherto known preparatory methods, for example by reacting a disuccinate with an amino-substituted benzonitrile, with difficulty and in low yield.

A process for the amination of aryl halides, which comprises reacting aryl halides with amines in the presence of a polar organic solvent, is disclosed in U.S. Pat. No. 3,484,487. This process is carried out under elevated pressure in the range from 34.5 to 103.5 bar (500–1500 psi) and in the temperature range from 250° to 280° C.

Surprisingly, it has now been found that aminated diketobis(aryl or heteroaryl)pyrrolopyrroles can be obtained in good yield by reacting halogenated diketobis(aryl or heteroaryl)pyrrolopyrroles with secondary amines, in the presence of an anhydrous, dipolar aprotic solvent and a base, under a pressure in the range from 0 to 10 bar, preferably from 1 to 3 bar, and in the temperature range from 50° to 230° C.

U.S. Pat. No. 4,632,893 teaches that 1,4-dithioketopyrrolo[3,4-c]pyrroles are suitable for use as photoconductive substances, especially in the near infrared range. Surprisingly, it has now additionally been found that the aminated 1,4-diketo-3,6-bis(aryl or heteroarly)pyrrolo[3,4-c]pyrroles obtained by the novel process of this invention also have photoconductive properties, not in the near infrared range, but in the wavelength range of visible light.

Accordingly, the present invention relates to a process for the preparation of compounds of formula

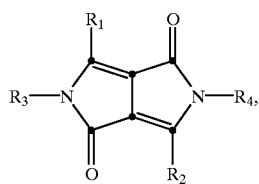

(I)

wherein $R_1$ is a group selected from

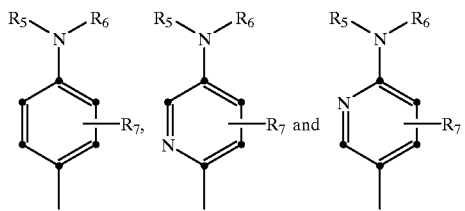

$R_2$ is a group selected from

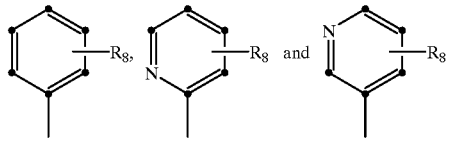

or has the same meaning as $R_1$; $R_3$ and $R_4$ are each independently of the other hydrogen, $C_1$–$C_{18}$alkyl, carbamoyl, $C_2$–$C_{13}$alkylcarbamoyl, $C_3$–$C_{25}$dialkylcarbamoyl, unsubstituted phenyl or benzyl, or phenyl or benzyl each substituted by halogen, $C_1$–$C_{12}$alkyl, $C_1$–$C_{12}$alkoxy, cyano or nitro, $R_5$ and $R_6$ are each independently of the other $C_1$–$C_{18}$alkyl, unsubstituted or substituted by —OH or —SH, or halogen-, $C_1$–$C_{12}$alkyl-, $C_1$–$C_{12}$alkoxy-, cyano- or nitro-substituted phenyl, or benzyl or phenylethyl, or —$NR_5R_6$ is a 5- or 6-membered heterocyclic radical selected from the group consisting of pyrrolidinyl, piperidyl, pyrrolyl, triazolyl, imidazolyl, pyrazolyl, piperazinyl, morpholinyl and thiomorpholinyl, and $R_7$ and $R_8$ are each independently of the other hydrogen, halogen, $C_1$–$C_{12}$alkyl, $C_1$–$C_{12}$alkoxy or cyano, which process comprises reacting a pyrrolopyrrole of formula

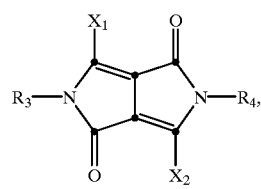

(II)

wherein $X_1$ is a group selected from

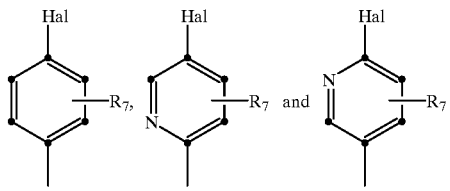

$X_2$ is a group selected from

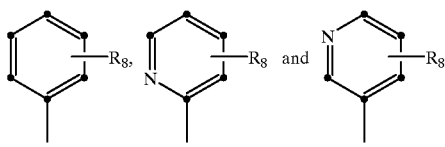

or has the same meaning as $X_1$, Hal is chloro, bromo, iodo or fluoro, and $R_3$, $R_4$, $R_7$ and $R_8$ are as defined above, with a secondary amine of formula

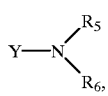

(III)

wherein Y is hydrogen or an alkali metal, and $R_5$ and $R_6$ are as defined above, in the molar ratio 1:1 or, if $X_2$ has the same meaning as $X_1$, in the molar ratio 1:2, in the presence of an anhydrous dipolar aprotic solvent and of an amount 0.1 to 15 times in excess of stoichiometric proportion, based on the amine of formula III, of an anhydrous organic base, in the temperature range from 50° to 230° C. and under a pressure from 0 to 10 bar.

Halogen will be understood as meaning, for example, iodo, fluoro and, preferably, chloro and bromo.

Examples of $C_1$–$C_{12}$alkyl groups are methyl, ethyl, n-propyl, isopropyl, n-butyl, sec-butyl, tert-butyl, n-pentyl, tert-amyl, n-hexyl, 1,1,3,3-tetramethyl, n-heptyl, n-octyl, nonyl, decyl, undecyl, dodecyl; and $C_1$–$C_{18}$ alkyl groups are in addition, for example, tridecyl, tetradecyl, hexadecyl and octadecyl.

Examples of $C_2$–$C_{13}$alkylcarbamoyl groups are N-methylcarbamoyl, N-ethylcarbamoyl, N-n-propylcarbamoyl, N-isopropylcarbamoyl, N-n-butylcarbamoyl, N-tert-butylcarbamoyl, N-n-pentylcarbamoyl, N-tert-amylcarbamoyl, N-hexylcarbamoyl, N-octylcarbamoyl, N-decylcarbamoyl and N-dodecylcarbamoyl.

Examples of $C_3$–$C_{25}$dialkylcarbamoyl groups are N,N-dimethylcarbamoyl, N,N-diethylcarbamoyl, N,N-dibutylcarbamoyl, N,N-dihexylcarbamoyl, N,N-didecylcarbamoyl and N,N-didodecylcarbamoyl.

Examples of $C_1$–$C_{12}$alkoxy groups are methoxy, ethoxy, propoxy, isopropoxy, n-butoxy, sec-butoxy, tert-butoxy, n-pentyloxy, tert-amyloxy, n-hexyloxy, n-heptyloxy, n-octyloxy, decyloxy and dodecyloxy.

Examples of $C_5$–$C_6$cycloalkyl groups are cyclopentyl and, in particular, cyclohexyl.

An alkali metal Y is, for example, lithium, potassium or, preferably, sodium.

It is preferred to carry out the process of this invention for the preparation of compounds of formula

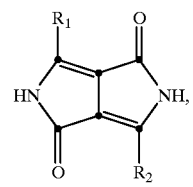

(IV)

wherein $R_1$ is a group

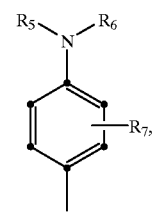

and $R_2$ is a group

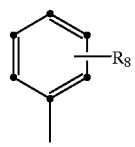

or has the meaning of $R_1$, in which formulae above $R_5$ and $R_6$ are identical and are $C_1$–$C_{12}$alkyl, 2-hydroxyethyl, 2-mercaptoethyl, cyclohexyl, benzyl or phenylethyl, or —$NR_5R_6$ is pyrrolidinyl, piperidyl, morpholinyl or thiomorpholinyl, and $R_7$ and $R_8$ are each independently of the other hydrogen, chloro, bromo, $C_1$–$C_4$alkyl or $C_1$–$C_4$alkoxy, by reacting a pyrrolopyrrole of formula

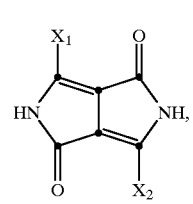

(V)

wherein $X_1$ is a group

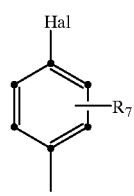

and $X_2$ is a group

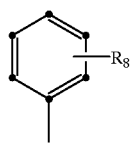

or has the same meaning as $X_1$, and Hal is chloro or bromo, and $R_7$ and $R_8$ have the preferred meanings given above, with a secondary amine of formula

(VI)

wherein $R_5$ and $R_6$ have the preferred meanings given above, in the temperature range from 100° to 220° C. and under a pressure in the range from 1 to 3 bar.

An especially preferred embodiment of the process of this invention in its above described preferred aspect is that wherein $R_1$ and $R_2$ in formula IV and hence $X_1$ and $X_2$ in formula V are identical, $R_5$ and $R_6$ in formula VI are $C_1$–$C_4$alkyl, 2-hydroxyethyl, 2-mercaptoethyl, or —$NR_5R_6$ is pyrrolidinyl, piperidinyl, morpholinyl or thiomorpholinyl, $R_7$ and $R_8$ are hydrogen, and Hal is chloro or bromo, and the reaction is carried out in the temperature range from 150° to 200° C.

It is most preferred to carry out the process of this invention for the preparation of compounds of formula IV, wherein $R_1$ and $R_2$ are identical and are each a group selected from

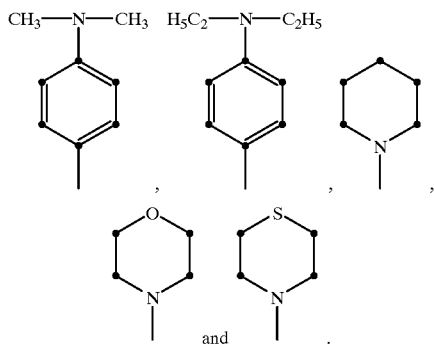

As suitable base it is possible to use any anhydrous organic base such as quinoline or, preferably, an excess of the amine used for the amination. The base will preferably be used in an amount 0.5 to 15 times in excess of stoichiometric proportion, based on the amine used for the amination.

Examples of suitable solvents are anhydrous, dipolar aprotic solvents such as carboxamides, lactams, urea derivatives, sulfones and nitrobenzene. Preferred solvents are dimethyl formamide, dimethyl acetamide, N-methylpyrrolidone, N,N'-dimethylethylene urea and N,N'-dimethylpropylene urea.

In accordance with the teaching of the cited U.S. patent specifications, the compounds of formula I can be used as pigments. They can, however, also be used as starting materials for the preparation of dithioketopyrrolo[3,4-c] pyrroles in accordance with U.S. Pat. No. 4,632,893.

The compounds of formula I are of particular interest for use as photoconductive substances in electrophotographic photoreceptors. Such photoreceptors consist of a conductive substrate and a photoconductor which is insulating in the dark but becomes conductive on exposure to light. The photoconductor can consist of one or more layers. If the photoconductor consists of a single layer, at least one photoconductive substance is dispersed in at least one binder or is deposited direct on to a conductive substrate by evaporation. A multilayer photoconductor preferably consists of at least one photoconductive layer which contains one or more photoconductive substances, and at least one charge-carrying layer.

The present invention accordingly also provides an electrophotographic photoreceptor comprising at least one conductive substrate, a photo- conductive layer and a charge-carrying layer, at least one of which layers contains at least one compound of formula IV.

The conductive substrate can be a metal plate or foil which is untreated or has been pretreated, for example by roughening, and for example consists of aluminium, zinc, magnesium, copper or an alloy of these metals. In the case of aluminium, the pretreatment can take the form of anodising. Suitable substrates are also vapour-blasted aluminium plastic sheets as well as polymer films having a metallised surface.

The photoconductor contains at least one compound of formula I as photoconductive substance and, as charge-carrying substances, compounds such as hydrazones or pyrazolines dissolved in polymer binders. Such a structure, after prior static charging and imagewise exposure, permits the formation of a corresponding pattern of charged and discharged areas (latent image), which can be transformed by known reprographic methods into a visible image.

The exposure can be to light in the visible wavelength region.

The compounds of formula I have a high dark resistance, which helps to preserve the static potential in areas which are not exposed to light.

If the photoconductor consists of a single layer, this layer contains one or more compounds of formula I, desirably in finely dispersed form, if desired together with charge-carrying substances, in an organic binder. The binder is preferably film-forming, insulating and adhesive. Depending on the utility, it is soluble in organic solvents or in basic mixtures of organic solvents which may contain water. Particularly suitable binders are those based on polycondensates or polyadducts such as polyamides, polyurethanes, polyesters, epoxy resins, phenoxy resins, polyketones, polycarbonates, polyvinyl ketones, polystyrenes, polyvinylcarbazoles, polyacrylamides, polymethyl methacrylates, polyvinyl butyrates, polyvinyl chlorides and also copolymers, for example styrene/maleic anhydride copolymers, styrene/methacrylic acid/methacrylate copolymers or vinyl chloride/vinyl accetate copolymers.

If the photoconductor consists of a plurality of layers, double layers are of particular interest. In this case, a photoconductive layer is first applied to the conductive substrate and a second, charge-carrying layer is then applied to the photoconductive layer. The layers can also be applied in the reverse order. One of the layers, preferably the charge-carrying layer, contains at least one compound of formula I. This compound can be dissolved or finely dispersed in an organic binder. Application to the conductive substrate is effected, for example, by applying a solution or dispersion of the binder/colorant mixture in an organic solvent and subsequently evaporating the solvent. However, the compound of formula I can also be applied to the conductive substrate by vapour deposition.

The second layer contains one or more charge-carrying substances, preferably dissolved or dispersed in an organic binder. Suitable charge-carrying substances are the most diverse aromatic, preferably nitrogen-containing, compounds, such as hydrazones or aromatic amines, which may contain alkylidene bridges or radicals. These substances are, for example, the substances described in German Offenlegungsschrift 3 447 685 on pages 57–65, and in the publication "Japan, Hardcopy '88, Post-International Symposium in Kansa; Recent Progress in Hardcopy Materials in Electrophotography", page 22 (Osaka, JP, 23.5.88).

The invention thus also relates to the preparation of an electrophotographic photoreceptor, which comprises applying a compound of formula I to a conductive base by means of an organic binder or by vapour deposition under vacuum, and subsequently forming a second, charge-carrying layer which contains an aromatic, nitrogen-containing compound.

To improve the physical properties of the layers, the photoconductive layer and the charge-carrying layer can also contain modifiers such as levelling agents, surfactants or plasticisers.

The invention is illustrated by the following Examples.

EXAMPLE 1

Under nitrogen, 20 g of 1,4-diketo-3,6-bis(4-bromophenyl)pyrrolo[3,4-c]pyrrole, 16.7 g of gaseous dimethylamine and 400 ml of anhydrous N-methylpyrrolidone are charged to a 1 liter steel autoclave. With moderate stirring, the suspension is heated for about 75 minutes to 180° C. and kept for 10 hours at this temperature. The pressure during this time is ca. 1 bar. The reaction mass is then cooled to room temperature, the autoclave is opened, and the suspension is filtered with suction. The filter cake is washed thoroughly in succession with dimethyl formamide, methanol and warm water, and the resultant moist pigment is dried at ca. 80° C. in a vacuum drier, affording 11.6 g (69.3% of theory) of the compound of formula

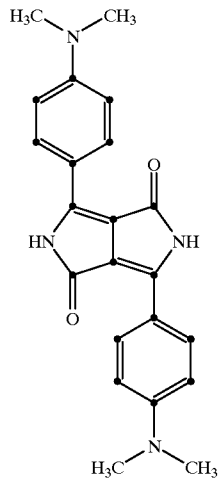

in the form of a bluish-violet powder.

EXAMPLE 2

The procedure Example 1 is repeated, using 25.9 g of anhydrous pyrrolidine instead of 16.7 g of gaseous dimethylamine and heating to 200° C. instead of only to 180° C. The pressure is ca. 2 bar. Yield: 11.56 g (60.5% of theory) of the compound of formula

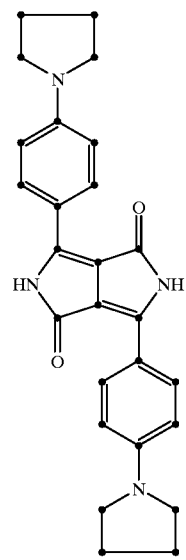

in the form of a bluish-violet powder.

EXAMPLE 3

The procedure of Example 1 is repeated, using 31 g of anhydrous piperidine instead of 16.7 g of gaseous dimethylamine and heating for 15 hours instead of 10 hours to 180° C. The pressure is ca. 1 bar. Yield: 10.6 g (52.1% of theory) of the compound of formula

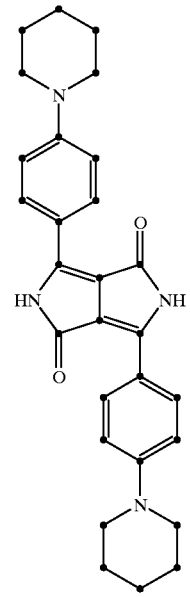

in the form of a violet powder.

EXAMPLE 4

The procedure of Example 1 is repeated, using 31.7 g of anhydrous morpholine instead of 16.7 g of gaseous dimethylamine and heating for 10 hours to 220° C. instead of 180° C. The pressure is ca. 2 bar. Yield: 10.2 g (49.7% of theory) of the compound of formula

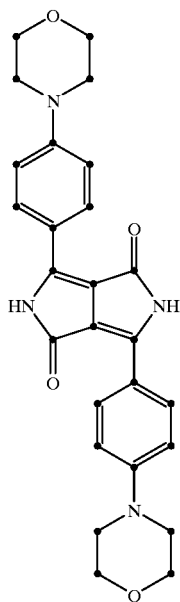

in the form of a violet powder.

EXAMPLE 5

Under nitrogen, 25 g of 1,4-diketo-3,6-bis(4-chlorophenyl)pyrrolo[3,4-c]pyrrole, 40.2 g of anhydrous pyrrolidine and 500 ml of andhydrous N,N'-dimethylethylene urea are charged to a 1 liter steel autoclave. With moderate stirring, the suspension is heated over ca. 2½ hours to 200° C. and kept for 10 hours at this temperature. The pressure during this time is ca. 2 bar. The reaction mass is then cooled to room temperature and working up is carried out as described in Example 1, affording 13.62 g (45.6% of theory) of the same compound as in Example 2.

EXAMPLE 6

A small glass pressure reactor of 20 ml content (with safety valve for max. 10 bar pressure) is charged with 0.75 g of 1,4-diketo-3-(4-fluorophenyl)-6-phenylpyrrolo[3,4-c]pyrrole, 0.97 ml of piperidine and 11.3 ml of anhydrous dimethyl sulfoxide. The reactor is screwed shut at room temperature and heated, with stirring, to 160° C. (external temperature). (The reactor is revolved in a heating bath of ca. 160° C.) After stirring for 23 hours at this temperature, the reactor is cooled to room temperature, opened, and the resultant suspension is filtered. The precipitate is rinsed with a small amount of dimethyl sulfoxide and then washed with water, and dried in a vacuum drier at 60° C., affording 0.60 g (ca. 65% of theory) of a compound of formula

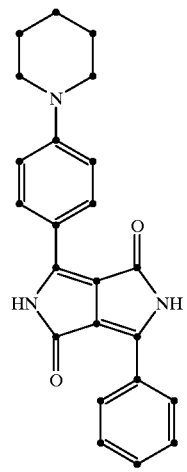

in the form of a reddish violet powder.

EXAMPLE 7

Under nitrogen, a 300 ml steel autoclave is charged with 5 g of 1,4-diketo-3,6-bis(4-bromophenyl)pyrrolo[3,4-c]pyrrole, 7.81 g of N-methylbutylamine and 100 ml of anhydrous N-methylpyrrolidone. With moderate stirring, the suspension is heated over ca. 2 hours to 200° C. and kept for 24 hours at this temperature. The pressure during this time is 1 to 2 bar. The reaction mass is then cooled to room temperature, the autoclave is opened, and the suspension is filtered with suction. The filter cake is washed thoroughly in succession with N-methylpyrrolidone and methanol, and the resultant moist pigment is dried at ca. 80° C. in a vacuum drier, affording 1.0 g (20% of theory) of the compound of formula

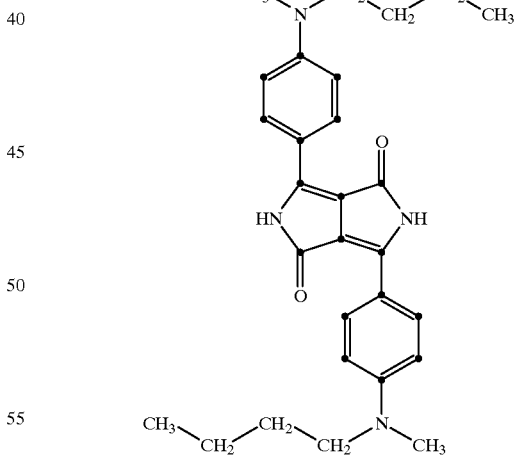

in the form of a bluish-violet powder.

EXAMPLE 8

0.3 g of the product of Example 1 is taken up in a mixture of 10 g of xylene and ethylene glycol monomethyl ether (2:1 by volume) containing 1.0 g of a commercially available alkyd/melamine resin (1:1 by weight). The suspension is then ground with glass beads for 5 hours and subsequently applied to an aluminium plate with a drawing rod (charge-carrying layer). This layer is dried for 3 hours at 50° C. The layer thickness is ca. 1 μm. A second layer consisting of a mixture of 0.6 g of a hydrazone of formula

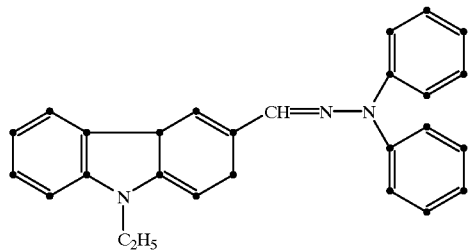

and 0.9 g of LUCITE® polyacrylate varnish 41 in 11 g of methyl ethyl ketone is then applied and dried for 15 hours at 50° C. The layer thickness is 1 to 15 μm. This photoreceptor has a sensitivity (E ½) of 5 μJ/cm$^2$, and can carry a 650 volt charge.

EXAMPLE 9

The product of Example 1 is applied to an aluminium substrate by vapour deposition at a rate of 5 Å/sec. under a vacuum of $10^{-6}$ mbar. The layer thickness is ca. 1000 Å. A second layer consisting of a mixture of 0.6 g of a hydrazone of formula

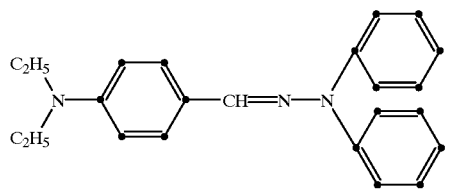

and 0.6 g of MAKROLON® polycarbonate (DuPont) in 10 g of tetrahydrofuran, is then applied and dried for 6 hours at 50° C. The layer thickness is ca. 15 μm. This photoreceptor has a light sensitivity (E ½) of 8 μJ/cm$^2$.

What is claimed is:

1. A process for the preparation of a compound of formula (IV)

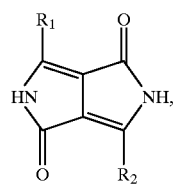

wherein $R_1$ is a group

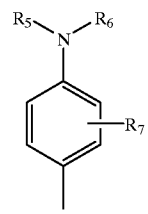

and $R_2$ is a group

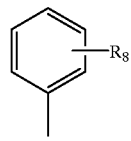

or has the meaning of $R_1$, in which formulae above $R_5$ and $R_6$ are identical and are $C_1-C_{12}$alkyl, 2-hydroxyethyl, 2-mercaptoethyl, cyclohexyl, benzyl or phenylethyl, or $-NR_5R_6$ is pyrrolidinyl, piperidyl, morpholinyl or thiomorpholinyl, and $R_7$ and $R_8$ are each independently of the other hydrogen, chloro, bromo, $C_1-C_4$alkyl or $C_1-C_4$alkoxy, which process comprises reacting a pyrrolopyrrole of formula (V)

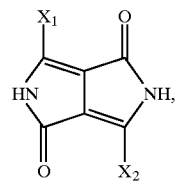

wherein $X_1$ is a group

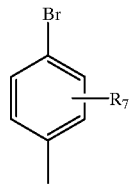

and $X_2$ is a group

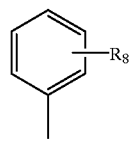

or has the same meaning as $X_1$, and $R_7$ and $R_8$ are defined hereinabove, with a secondary amine of formula (VI)

H—N(R$_5$)(R$_6$), wherein $R_5$ and $R_6$ are defined hereinabove in the molar ratio 1:1 or, if $X_2$ has the same meaning as $X_1$, in the molar ratio 1:2, in the presence of an anhydrous dipolar aprotic solvent and of an amount 0.1 to 15 times in excess of stoichiometric proportion, based on the amine of formula VI, of an anhydrous organic base, in the temperature range from 100° to 220° C. and under a pressure from 1 to 3 bar.

2. A process according to claim 1, wherein $R_1$ and $R_2$ in formula IV and hence $X_1$ and $X_2$ in formula V are identical, $R_5$ and $R_6$ in formula VI are $C_1-C_4$alkyl, 2-hydroxyethyl, 2-mercaptoethyl, or $-NR_5R_6$ is pyrrolidinyl, piperidinyl, morpholinyl or thiomorpholinyl, $R_7$ and $R_8$ are hydrogen, and the reaction is carried out in the temperature range from 150° to 200° C.

3. A process according to claim 1 for the preparation of a compound of formula IV, wherein $R_1$ and $R_2$ are identical and are each a group selected from

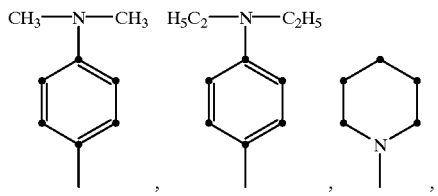

-continued

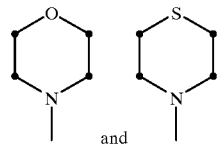

and

4. A process according to claim 1, wherein an excess of the amine of formula VI is used as base.

5. A process according to claim 1, wherein the solvent is a dipolar aprotic solvent selected from the group consisting of carboxamides, lactams, urea derivatives, sulfones and nitrobenzene.

6. A process according to claim 1, wherein the solvent is a dipolar aprotic solvent selected from the group consisting of dimethyl formamide, dimethyl acetamide, N-methylpyrrolidone, N,N'-dimethylethylene urea and N,N'-dimethylpropylene urea.

* * * * *